United States Patent [19]

Crippa

[11] 4,081,529
[45] Mar. 28, 1978

[54] POLYHYDROXYPHENYLCHROMANONES

[75] Inventor: Felice Crippa, Milan, Italy

[73] Assignee: Inverni Della Beffa S.P.A., Milan, Italy

[21] Appl. No.: 792,986

[22] Filed: May 2, 1977

[30] Foreign Application Priority Data

May 5, 1976 United Kingdom ............... 18415/76

[51] Int. Cl.² ..................... A61K 31/79; A61K 35/78; A61K 31/35
[52] U.S. Cl. ..................................... 424/80; 424/195; 424/283
[58] Field of Search ................................. 424/80, 283

[56] References Cited

U.S. PATENT DOCUMENTS 3,089,818   5/1963   Stone ....................................... 424/80
3,673,163   6/1972   Walkling ................................ 424/80

FOREIGN PATENT DOCUMENTS 1,139,939   11/1962   Germany.

OTHER PUBLICATIONS

Remington's Pharm. Sci., 15th Ed. (1975), Mack Publishing Co., Easton, Pa., pp. 1361 and 1245 and 1252.

Primary Examiner—Donald B. Moyer
Attorney, Agent, or Firm—Browdy and Neimark

[57] ABSTRACT

A process is described for producing a pharmaceutical product comprising a polyhydroxyphenyl chromanone obtainable from seeds of Silybum marianum which comprises forming a solution comprising said polyhydroxyphenyl chromanone and polyvinylpyrrolidone of molecular weight in the range from 3,000 to 40,000 in a solvent comprising water and a water-soluble organic solvent, the weight ratio of polyvinylpyrrolidone to polyhydroxyphenyl chromanone being from 0.5:1 to 4:1, and lyophilising said solution. Products may be so produced possessing excellent stability and which may be readily solubilised in aqueous media.

18 Claims, No Drawings

POLYHYDROXYPHENYLCHROMANONES

This invention relates to polyhydroxyphenyl chromanones obtainable from the seeds of *Silybum marianum*.

Extracts of seeds of *Silybum marianum* are known to possess antihepatotoxic activity due to their content of polyhydroxyphenyl chromanones, (G. Hahn et al., Arzneimittel - Forschung Drug Res. 18, 698–704, (1968).

Examples of these polyhydroxyphenyl chromanones include silybine (A. Pelter and R. Hansel, Tetrahedron Letters, 25, 2911–2916, (19); silydianine (D. J. Abraham, H. Wagner et al., Tetrahedron Letters 31, 2675–2678, (1970) and silycristine (H. Wagner et al, Tetrahedron Letters 22, 1895–1899, (1971).

The polyhydroxyphenyl chromanones obtainable from seeds of Silybum marianum are, however, highly insoluble in aqueous media and accordingly their use in the pharmaceutical field has been limited to oral formulations such as, for example, suspensions, tablets and sweets. It has been proposed to convert the polyhydroxyphenyl chromanones to water-soluble derivatives, for example, salts, but these derivatives suffer from the disadvantages of instability and also the properties of the parent polyhydroxyphenyl chromanones are frequently modified as a result of the conversion to derivatives.

We have now developed a process for converting polyhydroxyphenyl chromanones obtainable from seeds of *Silybum marianum* to a form which is both stable and soluble in aqueous media.

Thus according to the present invention there is provided a process for producing a pharmaceutical product comprising a polyhydroxyphenyl chromanone obtainable from seeds of *Silybum marianum* which comprises forming a solution comprising said polyhydroxyphenyl chromanone and polyvinylpyrrolidone of molecular weight in the range from 3,000 to 40,000 in a solvent comprising water and a water-soluble organic solvent, the weight ratio of polyvinylpyrrolidone to polyhydroxyphenyl chromanone being from 0.5:1 to 4:1, and lyophylising said solution.

Preferably, the solution which is subjected to lyophilisation contains a surface active agent, most preferably a non-ionic surface active agent. Examples of suitable non-ionic surface active agents are those of the "Polysorbate" type, i.e. fatty acid esters of sorbitol and its anhydrides copolymerised with ethylene oxide.

The solution of polyhydroxyphenyl chromanone and polyvinylpyrrolidone which is subjected to lyophilisation may conveniently be prepared by mixing a solution of the polyhydroxyphenyl chromanone in a water-soluble organic solvent with an aqueous solution of the polyvinylpyrrolidone. Examples of water-soluble organic solvents which may be employed in carrying out the method of the invention are cyclic ethers, such as, for example dioxan.

Water-soluble pharmaceutical products may be formed according to the invention for one or more individual polyhydroxyphenyl chromanones, for example from silybine, silydianine, silycristine or mixtures thereof or from polyhydroxyphenyl chromanone-containing extracts of Silybum marianum.

The lyophilised products obtained according to the invention are exceptionally stable and can be preserved for long periods of time without any apparent modification or degradation of the active principles. For example storage at 50° C for three months has been achieved without degradation.

The freeze-dried (lyophilised) products produced according to the invention can be readily re-dissolved in aqueous media, particularly solutions buffered to a pH between 7.6 and 8.0 to form pharmaceutical compositions in a form suitable for immediate use and the formation of such solutions forms a further aspect of the present invention. Where the reconstituted solution is for administration parenterally, it is of course important for the resultant aqueous medium to be sterile and pyrogen-free. Various procedures may be employed to redissolve the lyophilised products, for example, the products may be dissolved in a solvent mixture comprising water and one or more water-miscible organic solvents, the solvent mixture preferably being buffered to a pH between 7.6 and 7.8 and the resulting solution diluted with water or an aqueous buffer to provide a solution of the required concentration for pharmaceutical administration. Alternatively, particularly when a surface-active agent has been incorporated in the solution which is subjected to lyophilisation, the lyophilised product may be redissolved directly in an aqueous buffer, preferably a buffer having a pH of from 7.8 to 8.0. The reconstituted solutions so-formed have a high degree of stability.

The following examples illustrate the present invention:

EXAMPLE 1 — INJECTABLE PHIALS 30 g. of silybine were dissolved in 1,400 ml. of dioxan and 65 g. of polyvinylpyrrolidone of molecular weight 6,000 were dissolved in 500 ml. of water suitable for injection. The two solutions were combined and brought to a volume of 2,000 ml. with water suitable for injection. The solution thus obtained was freeze-dried as such (in bulk) or after distribution into phials made of dark glass, in amounts of 2 ml. per phial.

For reconstituting the contents of the phials it is possible to use 3 ml. of a solvent consisting of for example:

| | |
|---|---|
| Propylene glycol | 1.0 g. |
| Alcohol | 0.2 g. |
| Buffer solution in water at pH 7.8 q.s. | to 3 ml. |

One or more reconstituted phials can be diluted with 5% glucose solution and used for intraveinous injection.

EXAMPLE 2 — INJECTABLE PHIALS 30 g. of silydianine were dissolved in 1400 ml. of dioxan and 65 g. of polyvinylpyrrolidone of molecular weight 3,000 were dissolved in 500 ml. of water suitable for injection. The two solutions were combined and brought to volume of 2,000 ml. with water suitable for injection. The solution thus obtained was freeze-dried as such (in bulk) or after distribution into phials formed of dark glass, in amounts of 2 ml. per phial.

For reconstituting the phials it is possible to use for example 3 ml. of the solution referred to in Example 1.

One or more reconstituted phials can be diluted with 5% glucose solution and used for intraveinous injection.

EXAMPLE 3 — INJECTABLE PHIALS 30 g. of silybine were dissolved in 1,200 ml. of dioxan and 70 g. of polyvinylpyrrolidone of molecular weight 6,000 were dissolved in 500 ml. of water suitable for injection. The two solutions were combined and 110 g. of polyoxyethylene (20) sorbitan mono-oleate (referred to in the U.S. Pharmacopeia as "Polysorbate 80" and obtainable under the Registered Trade Mark TWEEN 80) added, the mixture agitated well and brought to a volume of 2,000 ml. with water suitable for injection.

The solution thus obtained was freeze-dried as such (in bulk) or after distribution into phials formed of dark glass, in amounts of 2 ml. per phial.

For reconstituting the phials it is possible to use 3 ml. of aqueous buffer solution at pH 8.

One or more reconstituted phials can be diluted in physiological solution and used for intravenous injection.

EXAMPLE 4 — INJECTABLE PHIALS 35 g. of dry extract of Silybum marianum containing 80% of polyhydroxyphenyl chromanonic substances were dissolved in 1,200 ml. of dioxan and 70 g. of polyvinylpyrrolidone of molecular weight 6,000 dissolved in 500 ml. of water suitable for injection. The two solutions were combined and 110 g. of polyoxyethylene (20) sorbitan mono-oleate added, the mixture agitated well and brought to a volume of 2,000 ml. with water suitable for injection.

The solution thus obtained was freeze-dried as such (in bulk) or after distribution into phials formed of dark glass, in amounts of 2 ml. per phial.

For reconstituting the phials it is possible to use 3 ml. of aqueous buffer solution at pH 8.

EXAMPLE 5 — INJECTABLE PHIALS 75 g. of silybine were dissolved in 3,250 ml. of dioxan and 172.5 g. of polyvinylpyrrolidone of molecular weight 3,000 dissolved in 1,250 ml. of water suitable for injection. The two solutions were combined and brought to a volume of 5,000 ml. with water suitable for injection. The solution thus obtained was freeze-dried as such (in bulk) or after distribution into phials formed of dark glass in amounts of 5 ml. per phial. For the reconstituting of the phials it is possible to use 5 ml. of a solvent constituted for example by:

| Propylene glycol | 1.70 g. |
| Ethyl alcohol | 0.33 g. |
| Buffer solution in water at pH 7.8 q.s. to | 5 ml. |

EXAMPLE 6 — POTABLE SOLUTIONS 190 mg. of the freeze-dried product obtained according to Example 1 (equal to 60 mg. of silybine) were dissolved immediately prior to use in 10 ml. of a solution having a pH between 7.2 and 7.4 and containing:

| Sugar | 2 g. |
| Propylene glycol | 1.5 g. |
| Ethyl alcohol | 2 g. |
| Water | q.s. to 10 ml. |

(It is possible to add other products endowed with choleretic, cholagogic or slightly laxative activity such as extracts of boldo, artichoke or rhubarb to this solution).

EXAMPLE 7 — POTABLE PHIALOIDS 420 mg. of freeze-dried product equal to 60 mg. of silibine and obtained according to the procedure of Example 3 were dissolved immediately prior to use in 10 ml. of a solution containing:

| Sugar | | 3 g. |
| Water buffered to pH 8 | q.s. to | 10 ml. |

(It is possible to add other products endowed with choleretic, cholagogic or slightly laxative activity such as extracts of boldo, artichoke or rhubarb to this solution.)

EXAMPLE 8 — POTABLE SOLUTIONS 7 g. of dry extract of Silybum marianum containing 80% of polyhydroxyphenyl chromanonic substances were dissolved in 245 ml. of dioxan and 14 g. of polyvinylpyrrolidone of molecular weight 40,000 were dissolved in 100 ml. of purified water. The two solutions were combined and brought to a volume of 400 ml. with purified water. The solution thus obtained was freeze-dried.

210 mg. portions of this freeze-dried product (equal to 70 mg. of dry extract of Silybum marianum) were distributed in small bottles or impermeable sachets. To dissolve the product at the moment of use it is possible to use, for example, 10 ml. of the solution described in Example 6.

EXAMPLE 9 — POTABLE THIALOIDS 7 g. of dry extract of Silybum marianum containing 80% of polyhydroxyphenyl chromanonic substances were dissolved in 245 ml. of dioxan and 14 g. of polyvinylpyrrolidone of molecular weight 17,000 are dissolved in 100 ml. of purified water. The two solutions were combined and 21 g. of polyoxyethylene (20) sorbitan mono-oleate added. The mixture was agitated well and brought to a volume of 400 ml. with purified water. The solution was freeze-dried.

420 mg. portions of this freeze-dried substance (equal to 70 mg. of dry extract of Silybum marianum) were distributed in small bottles or impermeable sachets. To dissolve the product at the moment of use it is possible to use for example 10 ml. of the solution described in Example 6.

EXAMPLE 10 — INJECTABLE PHIALS 15 g. of silybine and 15 g. of silydianine were dissolved in 1,400 ml. of dioxan and 65 g. of polyvinyl pyrrolidone of molecular weight 3,000 dissolved in 500 ml. of water suitable for injection. The two solutions were united and brought to a volume of 2,000 ml. with water suitable for injection. The procedure described in Example 1 was then followed.

EXAMPLE 11 — INJECTABLE PHIALS 12 g. of silybine and 18 g. of silydianine were dissolved in 1,400 ml. of dioxan, and the procedure of Example 10 followed.

EXAMPLE 12 — INJECTABLE PHIALS 18 g. of silybine and 12 g. of silydianine were dissolved in 1,400 ml of dioxan, and the procedure of Example 10 followed.

EXAMPLE 13 — INJECTABLE PHIALS 30 g. of silydianine or silybine were dissolved in 1,000 ml. of tetrahydrofuran and 65 g. of polyvinyl pyrrolidone of molecular weight 3,000 dissolved in 500 ml. of water suitable for injection. The two solutions were united and brought to a volume of 2,000 ml. with water suitable for injection. The solution thus obtained was freeze-dried as such (in bulk) or after distribution into dark glass phials, at the dosage of 2 ml. per phial.

For reconstituting the phial it is possible to use for example 3 ml. of the solution described in Example 1.

EXAMPLE 14 — INJECTABLE PHIALS 10 g. of silybine, 10 g. of silydianine and 10 g. of silycristine were dissolved in 1,400 ml. of dioxan and 65 g. of polyvinyl pyrrolidone of molecular weight 3,000 were dissolved in 500 ml. of water suitable for injection. The two solutions were united and brought to a volume of 2,000 ml. with water suitable for injection. The procedure of Example 1 was then followed.

The stability of products produced in accordance with the method of the invention is shown by the data in the following table.

Phials containing a water-soluble product formed from silybine according to the method of the invention were stored at a temperature of 50° C and at room temperature for periods ranging from one month to one year. At the end of the period, the phial contents were analysed for their content of the active ingredient. For comparison purposes, phials containing a freeze-dried product formed from an aqueous solution of a water-soluble silybine salt, namely the N-methylglucamine salt of silybine.

| Storage time | A | B |
|---|---|---|
| Zero time | 32 mg./phial | 30 mg./phial |
| 1 month at 50° C. | 30.1 mg./phial | 23.75 mg./phial |
| 2 months at 50° C. | 29.5 mg./phial | 20 mg./phial |
| 3 months at 50° C. | 30.05 mg./phial | 18 mg./phial |
| 1 year at room temp. | 30 mg./phial | 22 mg./phial |
| 2 years at room temp. | 30 mg./phial | 19 mg./phial |

A = Injectable phials of silybine prepared according to Example 1.
B = Phials containing freeze-dried water-soluble N-methyl glucamine salt of silybine.

The results show the enhanced stability of the product formed by the process of the invention.

I claim:

1. A process for producing a stable, water-soluble pharmaceutical product of one or more polyhydroxyphenyl chromanones selected from the group consisting of silybine, silydianine, silycristine and natural and reconstituted mixtures thereof which comprises forming a solution comprising said polyhydroxyphenyl chromanone and polyvinylpyrrolidone of molecular weight in the range from 3,000 to 40,000 in a solvent consisting essentially of water and a water-soluble organic solvent, the weight ratio of polyvinylpyrrolidone to polyhydroxyphenyl chromanone being from 0.1:1 to 4:1, and lyophilizing said solution.

2. A process as claimed in claim 1 wherein the solution which is subjected to lyophilisation contains a surface active agent.

3. A process as claimed in claim 1 wherein the surface active agent is non-ionic.

4. A process according to claim 1 wherein the solution which is subjected to lyophilisation is formed by mixing a solution of the polyhydroxyphenyl chromanone in a water-soluble organic solvent with an aqueous solution of the polyvinylpyrrolidone.

5. A process according to claim 1 wherein the weight ratio of polyvinylpyrrolidone to polyhydroxyphenyl chromanone is greater than 1:1.

6. A process according to claim 5 wherein the weight ratio of polyvinylpyrrolidone to polyhydroxyphenyl chromanone is greater than 2:1.

7. A pharmaceutical product whenever produced by a process according to claim 1.

8. A process for producing a pharmaceutically acceptable aqueous solution of one or more polyhydroxyphenyl chromanones selected from the group consisting of silybine, silydianine, silycristine and natural and reconstituted mixtures thereof, which comprises reconstituting a product according to claim 7 in a pharmaceutically acceptable aqueous excipient.

9. A process according to claim 8 in which the aqueous solution is sterile and pyrogen-free.

10. A process according to claim 8 in which said product is dissolved in an aqueous medium buffered to a pH between 7.6 and 8.0.

11. A process according to claim 10 in which said product is dissolved in a solvent mixture comprising water and a water-miscible organic solvent and the resulting solution is diluted with water.

12. A process according to claim 11 wherein the solvent mixture is buffered to a pH between 7.6 and 7.8.

13. A process according to claim 10 in which said product is dissolved in an aqueous buffer.

14. A process according to claim 13 in which the solution subjected to lyophilisation to form said product contained a surface-active agent.

15. A process according to claim 13 in which said aqueous buffer has a pH of from 7.8 to 8.0.

16. A process for producing a stable, water-soluble pharmaceutical product comprising one or more polyhydroxyphenyl chromanones selected from the group consisting of silybine, silydianine, silycristine and natural and reconstituted mixtures thereof which comprises forming a solution comprising said polyhydroxyphenyl chromanone and polyvinylpyrrolidone of molecular weight in the range from 3,000 to 40,000 in a solvent consisting essentially of water and a water-soluble organic solvent selected from the group consisting of dioxan and tetrahydro furan, the weight ratio of polyvinylpyrrolidone to polyhydroxyphenyl chromanone being from 0.1:1 to 4:1 and lyophilizing said solution.

17. A pharmaceutical product produced by the process of claim 2.

18. A pharmaceutical product produced by the process of claim 8.

* * * * *